United States Patent [19]

Staab

[11] Patent Number: 5,529,782
[45] Date of Patent: Jun. 25, 1996

[54] DISSOLVABLE DEVICE FOR CONTRACEPTION OR DELIVERY OF MEDICATION

[76] Inventor: Robert Staab, 73 Franklin TPK, Allendale, N.J. 07463

[21] Appl. No.: 333,717

[22] Filed: Nov. 3, 1994

Related U.S. Application Data

[60] Division of Ser. No. 68,778, Jun. 1, 1993, Pat. No. 5,393,528, which is a continuation-in-part of Ser. No. 880,093, May 7, 1992, abandoned.

[51] Int. Cl.⁶ .............................. A61F 9/02; A61F 13/15; A61F 13/20; A01N 25/08
[52] U.S. Cl. ................ 424/436; 424/409; 424/430; 424/431; 424/432; 424/433; 424/445; 424/DIG. 14; 514/772.3; 514/777; 514/781; 514/784; 514/785; 514/841; 514/843; 514/953; 514/967; 604/358; 604/378; 604/904
[58] Field of Search ...................... 424/409, 430, 424/431, 432, 433, 436, 445, DIG. 14; 514/772.3, 777, 781, 784, 785, 841, 843, 953, 967; 604/358, 378, 904

[56] References Cited

U.S. PATENT DOCUMENTS

| | | | |
|---|---|---|---|
| 4,304,591 | 12/1981 | Mueller et al. | 424/433 |
| 4,707,362 | 11/1987 | Nuwayser | 424/433 |
| 5,071,648 | 12/1991 | Rosenblatt | 424/78.06 |

FOREIGN PATENT DOCUMENTS

| | | |
|---|---|---|
| 0050480 | 4/1982 | European Pat. Off. . |
| 2094711 | 2/1972 | France . |

Primary Examiner—Carlos Azpuru
Attorney, Agent, or Firm—Evelyn M. Sommer

[57] ABSTRACT

A dissolvable element containing an agent material is used for local administration of the agent material in an internal body area. The dissolvable element is made of dissolvable polymer material and/or complex carbohydrate material which are food grade materials and have selected dissolving properties, such that it remains in substantially solid form before use, and dissolves due to human body temperatures and moisture during use to release the agent material in a desired timed release and dosage. As a contraceptive, the dissolvable element is preferably a film made of polyvinyl alcohol, polyethylene oxide, hydroxypropyl methyl cellulose and/or carboxymethyl cellulose. The dissolvable element may be formed as a laminate of different film layers for compound release properties, or it may be ground into particles and incorporated in a tampon or suppository. The dissolvable element may be foamed as a means for increasing its dissolution rate. The agent material can be a spermicide, such as Nonoxynol-9, and/or a drug or medication. The device of the invention can also be applied topically as for example in the treatment of wounds, burns and ulcers, as well as to treat, irritations, Herpes, and ulcerations and blisters of the oral cavity. It is also possible to prepare dressings in which the dissolvable element of the invention comprises the bottom most layer. This permits painless application of medication to wounds.

13 Claims, 2 Drawing Sheets

DISSOLVABLE DEVICE FOR CONTRACEPTION OR DELIVERY OF MEDICATION

This application is a division of application Ser. No. 08/068,778 filed Jun. 1, 1993, now issued to U.S. Pat. No. 5,393,528 which in turn was a continuation-in-part of application Ser. No. 07/880,093 filed May 7, 1992 now abandoned.

FIELD OF THE INVENTION

This invention generally relates to a dissolvable device for use as a contraceptive or for internal delivery of medication, and more particularly, to films made of a safe, polymer material incorporating a spermicide and/or medication that is released by dissolution of the film over time. The films may be adapted for rapid dissolution (for example in 5–60 seconds) or for dissolution over prolonged periods (for example up to 12–24 hours).

BACKGROUND ART

Due to the growing awareness of medical complications associated with the use of oral contraceptives and intrauterine devices, interest in other contraceptive methods has increased. Other contraceptive methods presently in use include diaphragms, sponges, cervical caps, spermicidal creams, foams, and suppositories for women, and condoms for men. Diaphragms and cervical caps usually require fitting by trained medical personnel, and must be refitted or replaced on a regular basis. Sponges take up a relatively large volume, which may result in a feeling of discomfort. Chemical barrier contraceptives such as creams, foams, jellies, tablets, and suppositories are often inconvenient and messy to apply and use, and in some cases cause irritation. Condoms are considered inconvenient to use during sexual activity and interfere with the sensation of the users. Thus, all such contraceptive methods in current use cause some inconvenience to users and detract from the users' spontaneity or feeling of pleasure during sexual activity.

Moreover, it is often desirable to administer medication in the vagina or other internal areas of the body such as the mouth, rectum, nose, ear and eye. In the case of the vagina, medication can be administered, either in conjunction with use of a contraceptive device or separately. In the treatment of vaginal disorders, it is often desirable that the medication be applied throughout the areas of the vaginal tract and cervix over an extended period of time, for example, several hours or days. The remoter areas of the vaginal tract might not be readily reached by conventional vaginal suppositories due to the compact size and shape required for convenience of insertion. Also, because of the structure and shape of the vagina, inserted suppositories or tablets often do not stay in place, or, upon melting, the medication may drain out of the vaginal passage, thereby reducing the effectiveness of the applied medication. Medicated tampons also do not extend far enough or widely enough into the vaginal tract to deliver medication throughout the vaginal tract. Other types of rigid applicators have similar delivery problems and are uncomfortable to insert and use. Thus, under current methods, the desired medication may not be applied or maintained effectively in the vaginal tract for a sufficient period of time.

Figure 3:
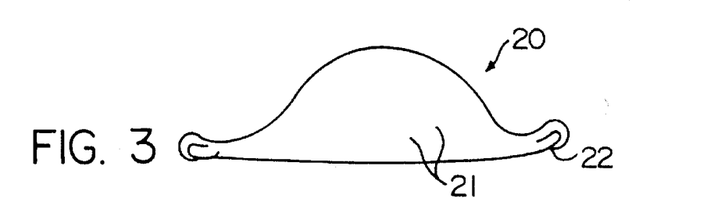
FIG. 3 shows a variation using the dissolvable film in a barrier contraceptive incorporating a dissolvable flexible rim for shape retention.

A recent commercial product is a contraceptive film sold under the name "VCF"0 by Apothecus, Inc., of Great Neck, N.Y. The VCF film is made of polyvinyl alcohol (PVA) and contains the spermicide called "Nonoxynol-9" and glycerine as a plasticizer material. However, the VCF film does not dissolve readily, and has poor stability in hot, humid environments. The texture of the film is relatively hard, and the film has a sharp edge. The film also delivers only 65 mg. of spermicide, which may be insufficient. It is also expensive to make and unlike a preferred embodiment of the present invention as illustrated in FIG. 3 infra, it has no capacity to be used as a barrier contraceptive.

More importantly, the VCF product suffers from deficiencies of all like prior art products in that it does not dissolve readily and in addition is not stable to prolonged storage at high temperature and high humidity, such as is generally encountered in numerous tropical third world countries as well as seasonally in more temperate climates. Such products become, under exposure to adverse humidity conditions, sticky and excessively hygroscopic. To resolve this problem, prior art devices, as typified by the VCF device, employ expensive protective packaging, such as foil-packs and the like. Such packaging greatly increases the cost of the product to the end user. The high cost discourages use in areas of the world where the product is most needed. Moreover, foil packaging increases package components and since the foils used are not readily decomposable in landfills, such packages have a disadvantaged environmental impact.

It should be noted that as used herein, high temperature means up to 140° F., high humidity means up to 99% relative humidity and prolonged storage means in excess of three years.

SUMMARY OF THE INVENTION

In accordance with the present invention, a device adapted for local administration of an agent material in an internal body area such as the vagina, rectum, oral cavity, nasal passages and the like, comprises a dissolvable element and an agent material carried in said dissolvable element, wherein said dissolvable element is made of dissolvable polymer material, particularly, a mixture of polyvinyl alcohol, polyethylene oxide, and/or complex carbohydrate material, which are selected such that the dissolvable element remains in solid form before use, and dissolves due to human body temperatures and moisture during use to release said agent material for local administration in the internal body area.

The preferred dissolvable element is a film made of polyvinyl alcohol, polyethylene oxide, and/or a complex carbohydrate material such as hydroxypropyl methyl cellulose which are safe, food-grade materials selected to obtain a desired release characteristic for the agent material. Two or more film layers may be combined as a laminate for compound release properties. Alternatively, a larger film layer or multiple laminates may be used as a barrier contraceptive. The dissolvable material may also be employed as an applicator tube for delivery of a contraceptive or delivery of medication or medical device. The dissolvable element dissolves within the body area so that it does not have to be physically removed after use. It can also dissolve completely when flushed away, so that no plumbing blockage or ecologically disturbing solid waste occurs.

The dissolution properties and texture of the dissolvable element may be modified by adding nitrogen or other suitable gases in forming the film, as well as the use of polyethylene oxide alone or in mixtures with polyvinyl alcohol and/or complex carbohydrate material. Forming the film in the invention with different film layers or polymer materials allows varied dissolution properties. The polyethylene oxide and complex carbohydrate materials add lubricity to the product as an added benefit. The composition of the dissolvable element is selected to have an improved heat and humidity stability, feel, texture, and dissolution time (2 to 3 times quicker) as compared to the conventional VCF film. The VCF film does not use gases to modify dissolution properties, nor does it use polyethylene oxide or complex carbohydrate materials either alone or in combination with polyvinyl alcohol to modify dissolution or texture. As compared to the invention, the VCF film also does not employ a laminate of dissolvable films for compound release properties, and cannot be used as a barrier contraceptive.

It should be noted that heretofore, the significance of the addition of gases in the formation of the film to alter the texture and solubility of the film has not been recognized.

The active agent(s) may be incorporated into either the entire portion of the device i.e., as a homogeneous blend or in the case of a laminate, the device may include a layer of active material, the other layer or layers containing different active materials or have been selected with a view to the overall dissolution properties.

As a contraceptive device, the dissolvable film incorporates a spermicide and is inserted by hand or by means of an applicator or inserter into the vaginal tract adjacent to the cervix. The contraceptive film is safe and fully dissolvable. It can be made at substantially lower cost and does not have the problems of removal, cleaning, reuse, and/or refitting as compared to conventional diaphragms and sponges. Alternatively, the film may be molded with a dissolvable flexible rim like a conventional diaphragm for greater expansion and retention in the area of the cervix.

The dissolvable element may also be in tubular form as a vaginal tampon, the dissolvable device being inserted within the vaginal cavity using an applicator, or as a suppository, or ground as timed-release powders filled into other delivery devices. It can also be used to deliver medications such as anti-infectives, anti-inflammatories, coronary vasodilators, anesthetics, antitussives, expectorants, estrogenic, progestational, or prostaglandin agents, and the like. It may include fragrance, flavorants, coloring agents, preservatives, etc., to provide a more acceptable, environmentally sound product for consumers, as well as a plasticizer or gas additive for better handling, lubricity, and/or release characteristics.

Other objects, features, and advantages of the present invention will become apparent from the following detailed description of the best mode of practicing the invention when considered in conjunction with the drawings as follows:

DESCRIPTION OF PREFERRED EMBODIMENTS

In the invention, a dissolvable device for contraception or delivery of medication contains a dissolvable element made of a dissolvable polymer material, particularly, a mixture of polyvinyl alcohol, polyethylene oxide, and/or complex carbohydrate material, used for local administration of a spermicide and/or medication agent in an internal body area. The dissolvable polymer material is preferably a food-grade material safe for internal use. The dissolvable element is designed to be heat stable (e.g., up to 140° F.), and humidity stable (e.g., up to 99% relative humidity) so as to remain in substantially solid form and not begin dissolving before its intended use. Lubricity is another desirable property for use in the vagina and other internal (e.g., rectal) areas where sensitive tissues are likely to be encountered.

The preferred dissolvable element is in the form of a film made of the combination of grades of polyvinyl alcohol, polyethylene oxide, and/or complex carbohydrate material. Polyvinyl alcohol (PVA) is a preferred material for the film because it is non-toxic and medically safe to use internally. PVA comes in different grades that can be classified as cold water soluble (dissolves from 40° to 212° F.), intermediate dissolving (110° to 212° F.), fully hydrolyzed (140° to 212° F.), and superhydrolyzed (180° to 212° F.). PVA is commercially available from companies such as Air Products Company, of Allentown, Pa. The cold water soluble and intermediate dissolving grades are the most useful for the desired moisture and heat- dissolving properties for contraceptive purposes. A particularly preferred cold water soluble grade of PVA is an 80% hydrolyzed polyvinyl alcohol having a molecular weight of 9,000–10,000; for intermediate solubility, an 87–89% hydrolyzed polyvinyl alcohol having a molecular weight of 13,000–23,000 for a slow dissolving, a 98–99% hydrolyzed polyvinyl alcohol having a molecular weight of 31,000–50,000 and for the least dissolving, a fully hydrolyzed >99% of polyvinyl alcohol having a molecular weight of 85,000–186,000 being preferred. All of the aforementioned polyvinyl alcohol preparations are available from Aldrich Chemical, Milkwaukee, Wis. However, in the invention, a film of the higher temperature or water soluble grade may be combined with a film of the lower temperature or water soluble grade in order to alter the temperature dissolution and moisture, solubility and stability properties so that the film can be used most suitably in the vaginal environment. The PVA material or materials are selected for contraceptive use to dissolve relatively quickly, e.g., over several minutes, or in some cases as low as several seconds. For use in delivering medications, the film composition may be selected for a longer release time, such as several days. In the case of medications to be administered via the oral cavity, it is advantageous that dissolution take place fairly rapidly.

Polyethylene oxide is another good material for the film because it has very good moisture, particularly humidity, stability and further is a food contact grade material. It is very compatible with the spermicide nonoxynol-9 and many other medications. It also has the added benefit of good lubricity, which makes the film structure even more comfortable to insert and use during sexual activity. Preferred polyethylene oxide materials are sold by Union Carbide Corp., of Danbury, Conn., in molecular weights of from 50,000 to 8,000,000 Daltons. The polyethylene oxide is available from Aldrich Chemical, Milwaukee, Wis.

The use of inert gases such as nitrogen, in forming the film to modify the dissolution properties of the dissolvable element formed from polyethylene oxide has been found to be equally favorable in this case as their use in connection with the polyvinyl alcohol films. The dissolution of the film can be readily adjusted by using different viscosities of the hydroxypropyl methyl cellulose ranging from less than 80 to more than 4,000 centipoises.

A complex carbohydrate material suitable for use in the film is hydroxypropyl methyl cellulose, or carboxy methyl cellulose which is sold, for example, under the trademark "Methocel" by Van Waters & Rogers, Inc., of Seattle, Wash. This material is also food-grade, medically safe to use internally, low cost, and very stable in a humid environment. "Methocel" is cellulosic in nature being derived from trees. It is dissolvable in the same temperature ranges as PVA. Hydroxypropyl methyl cellulose is a particularly preferred material for use in forming the films of the invention. Its acceptance by the FDA as a direct food additive is well known (CAS 9004-65-3). The preferred hydroxypropyl methyl cellulose has an average molecular weight of about 86,000.

The film may be a laminate of two or more layers of different polymer material's, or may be a single layer with two or more polymer ingredients mixed together. Further, the film laminate may be a gas foamed film or constructed of layers of different gas foamed films or of layers of both non-foamed and gas foamed films. The exact mixture used will depend upon the intended use and combination of qualities desired, which may include heat-dissolving temperature range, time release period, lubricity, shelf life, turgidity, stability in a moisture environment, compatibility with spermicides and/or medications etc. In the case of contraception, two films may be used which dissolve at varying rates. Such a laminate device can offer prompt efficacy upon insertion combined with extended contraceptive protection with dissolution taking place over a period of many hours. Thus in accordance with the invention, the film may be constructed as a laminate composed of gas foamed film with non-gas foamed film layers, polyvinyl alcohol and polyethylene oxide film layers, polyvinyl alcohol and hydroxypropyl methyl cellulose layers, in all possible combinations. The laminates can be formed in the conventional manner, for example the mixture in liquid form will be poured or cast on to a plate or into a mold and allowed to begin to set, at which time another liquid mixture of different composition will be poured on to the first setting up mixture, and both mixtures allowed to set up completely producing a laminate or layers of different materials.

Fully formed films can also be laminated to each other through use of an adhesive. A preferred adhesive is a dilute aqueous solution of the polymer from which the film has been made. Thus, for example, a polyvinyl alcohol film could be adhered to another polyvinyl alcohol film through use of a dilute solution of polyvinyl alcohol.

The agent material to be administered locally may be spermicide for contraceptive use, and/or drug or medication. The agent material is evenly distributed throughout the film, so that as the film slowly dissolves, it releases the agent material in the proper dosage to perform its spermicidal or medicating function. The agent material is selected for compatibility with the polymer material and its dissolution characteristics. The device of the invention thus is composed of a biologically compatible material that has been blended homogeneously with a spermicide or drug which is released into a body cavity at a controlled rate upon contact with the body fluid.

Some spermicides have good surfactant properties which facilitate dissolving and dispersing in vaginal fluids. Examples of those suitable for use include nonylphenoxypolyethoxy ethanol (sold under the trademark "Nonoxynol-9"), p-methanyl phenylpolyoxyethylene ether (Menfegol), polyoxyethylene oxypropylene stearate, polyoxethylene laureate, glycerol ricinolate, mono-iso-octyl phenyl ether, polyethylene glycol, methoxy polyoxyethylene glycol 500 laureate, polyoxyethylene stearylamine, benzalkonium chloride, cetyl trimethylammonium bromide, methyl benzethonium chloride, sodium dodecylsulfate, nonylphenol polyethylene sodium sulfate, sodium oleate, zinc phenosulfonate, dodecyl diaminoethyl glycine, p-diisobutylphenoxy polyethanol (Octoxynol), dodecamethylene glycol monolaureate, sodium lauryl sulfate and the like. A suitable dosage of nonoxynol-9 for contraceptive use is about 100 to 150 mg. However, the amount of spermicide may vary in accordance with their rate of release from the device and the spermicidal efficacy.

The dissolvable element may be used to deliver a medication internally in the vaginal or cervical area in combination with a spermicide or alone. Suitable medications which can be delivered with the film include: (1) anti-infectives such as antibiotics, sulfonamides, antivirals, antifungals, antiprotozoan and antibacterials; (2) anti-inflammatories, such as hydrocortisone, dexamethasone, triamcinolone, and various prednisolone compounds; (3) estrogenic steroids, such as estrone; (4) progestational agents, such as progesterone; (5) prostaglandins; (6) coronary vasodilators; (7) antitussives; (8) antihistamines; (9) anesthetics and (10) decongestants. Monoclonal antibodies such as those useful against cell surface components or against pathogenic organisms such as the human-immuno-deficiency (HIV) family of viruses may be incorporated into the device of the present invention for ultimate intravaginal release. Combinations of the various drugs may be used as desired. Typically the range of drug additives may be in the amount of 0.0001% to about 50% by weight. The medications may be in a variety of chemical forms, such as uncharged molecules, molecular complexes, or nonirritating, pharmacologically acceptable salts. Simple derivatives of such medications, such as ethers, esters, amides, and the like, can also be used for desirable properties such as retention, release, and easy hydrolyzation by body pH, enzymes, etc. The amount of medication to be used varies depending upon the particular drug, the desired therapeutic or prophylactic effect, and required release times. Other drugs include clotrimazole, miconazole, ticonazole, benzalkonium chloride, nystatin, dermally active steroids, hormones, benzocaine, sulfas, biologically prepared actives, decongestants, cough/cold remedies, psychotropics, nitroglycerine, etc. If the drug can be applied on or in a moist area of the body, such as the mouth, skin, vagina, rectum, ear canal, eye, etc., then the film can be used to deliver the drug effectively with timed release of the proper dosage. This should be an ideal way for treating ulcers of the mucous membranes and of the skin as well as treating burn wounds.

The dissolvable element may also include plasticizer material, such as water, glycols, glycerin, and like materials, in order to enhance lubricity and softness. While water is suitable as a plasticizer it is not useful in all cases, but this factor can be readily ascertained. A preferred plasticizer is glycerin USP, sold by Van Waters & Rogers, Inc., in either natural or synthetic form. Glycerine (glycerol) CAS 56-81-5 is particularly preferred. The plasticizer may be added in any desired concentration, for example, from 0.1% to 35%, for better handling and lubricity. The softness and flexibility of the dissolvable film, due to its thin layer structure without any rigid elements, and particularly when combined with plasticizer, ensures that the device may be worn with complete comfort and will not be felt by the sexual partners.

Various preservatives, antifungal agents, antibacterial agents, antiviral agents, antiprotozoal agents, and antioxidants may also be added if desired. Flavors, fragrances, and/or coloring agents may also be added. The polymer film may be substantially transparent, or may be embossed with indicia or colored with opaquing agents. These additives may be present in any desired concentration, for example, from 0.001% to 50%. The concentrations of these additives will depend upon the desired properties, the agent to be released, the potency, the desired dosage, dissolution times, etc.

In preparation, the polymer solids, water, or other solvent, contraceptive and/or medicinal, glycerine etc. are admixed in the proper concentrations and the mixture heated to the appropriate temperature for dissolution and formation of a uniform blend to take place. The heating can take place, for example, by submerging vessels containing the mixture in water or jacketed vessels held at constant temperature, for example 104°–140° F. The mixture can either be cast directly or transferred into another water bath of cooler temperature, for example 68°–104° F. and other heat sensitive ingredients introduced with stirring. The application of heat is, however, not necessary, which is advantageous when pharmaceuticals or other agents to be added are heat sensitive.

Several formulations utilizing different polymers as well as different active ingredients are listed below:

| I. Benzalkonium Film, 19 mg benzalkonium chloride | |
|---|---|
| hydroxypropyl methyl cellulose | 52.5% |
| glycerine | 37.5% |
| BZK* | 10.0% |
| | 100.0% |
| nitrogen gas added to form foamed web | <1.0% |

*BZK, e.g., BTC-50, a 50% aqueous active drug from Stepan Company, Northfield, Illinois.
Chemical, Jersey City, NJ

| II. Nonoxynol-9 Film, 100 mg nonoxynol-9 | |
|---|---|
| hydroxypropyl methyl cellulose | 36.0% |
| glycerine | 29.0% |
| nonoxynol-9* | 35.0% |
| | 100.0% |
| nitrogen gas added to form foamed web | |

*nonoxynol-9 from Rhone Poulenc, NJ

| III. Clotrimazole Film, 100 mg clotrimazole | |
|---|---|
| hydroxpropyl methyl cellulose | 36.0% |
| glycerine | 29.0% |
| clotrimazole* | 35.0% |
| | 100.0% |
| nitrogen gas added to form foamed web | |

*clotrimazole from e.g., Flavine, Inc. Closter, NJ

| IV. Vaginal Deodorant Film | |
|---|---|
| polyethylene oxide | 55.0% |
| glycerine | 35.0% |
| fragrance | 10.0% |
| | 100.0% |
| nitrogen gas added to form foamed web | |
| fragrance from e.g., IFF, Dayton, NJ | |

| V. Vaginal Lubricant | |
|---|---|
| polyethylene oxide | 75.0% |
| glycerine | 25.0% |
| | 100.0% |
| nitrogen gas added to form foamed web | |

The film characteristics may also be altered by adding appropriate amounts of gas, such as air, nitrogen, or other inert gases, which can produce a more acceptable film texture and modify the dissolution rates accordingly. For example, it has surprisingly been found that the addition of nitrogen or other inert gas to a PVA film containing nonoxynol-9 halves the dissolution rate of the film. The fine tuning of dissolution rates and delivery of agent material, by the addition of gases and by altering the grades or mixtures of polymer materials or layers, is an important aspect of the present invention.

On addition of the gas, preferably nitrogen, a web is formed of the final formulation and the gas. The resultant structure can be described as a foam with various sized air bubbles trapped in the matrix. There is a dual benefit that has been surprisingly observed in this connection, namely that not only can the size of the bubbles in the foam alter the dissolution rates and correct what is a serious flaw in standard polymer films, it also offers to the user a perceptible softness to the film which enables the delivery of many types of drugs to tender mucosal tissues. It has been observed that the formation of this web of the polymer/drug formulation and the gas must be made just prior to casting on the glass or steel plates. This offers precise control over the microbubbles and resultant control over the dissolution.

Without this web formation, the quick release of drug was heretofore not possible. This frothy foam mixture or web can also be added to a mold to provide a formed device such as a barrier delivery system which completely dissolves upon use in a body cavity, e.g. the vagina.

The gases, for example, air or nitrogen are introduced near the point of application of the liquid polymer material to the stainless steel casting sheet. The gases are added in a closed system by mixing with whipping blades or a motor driven homogenizer to homogenize the mixture of polymer, active material and gas to form a frothy foam. The final mixture then sets up or gels as a foam. It is also possible to pour the frothy foam mixture into a mold. The mold is then deformed and the formed device such as a diaphragm, is removed.

As a contraceptive, the film can be formed in a diaphragm shape or a sponge shape with the spermicide incorporated therein. The film can also function as a barrier to the cervical os. The user enjoys the benefit of not having to remove the device the morning after, and can remove the dissolved residue simply by douching or bathing. Any residue will dissolve completely when flushed away. Where the user discards a dissolvable diaphragm or sponge or an incompletely used film, no plumbing blockage or ecologically disturbing solid waste occurs.

Figure 1:
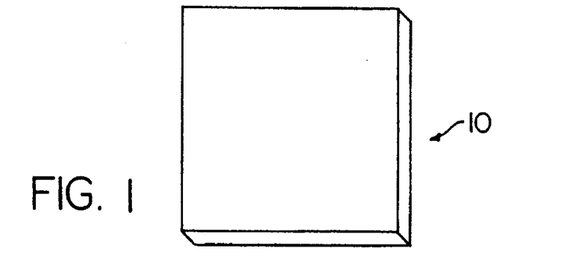
FIG. 1 is a schematic diagram of a dissolvable device in accordance with the present invention in the form of a contraceptive film.

Referring to FIG. 1, a preferred form of contraceptive and/or drug delivery device employs a single layer dissolvable film 10 having a shape and area of approximately 4 square inches by 3 mils thick. The agent is evenly dispersed throughout the film matrix and can dissolve once it is placed in a warm moist body cavity, e.g., the vagina. The film is intended to remain in solid form, for shelf storage or prior to use, at temperatures up to 140° F. Controlled environmental storage (temperature and humidity) of the film prior to use may be desirable if ambient temperatures and humidity are extreme. Once installed in the vaginal tract, the film will dissolve due to the moisture and body temperature in the vagina, typically 98.6° F. As the spermicide or drug is released from the dissolving film, it becomes mixed in the vaginal fluids and adheres to the tissues where it forms an effective matrix for drug action, e.g., spermicidal or anti-infective action. After use, the residual polymer, drug, and vaginal fluids are removed naturally from the body by washing.

Figure 2:
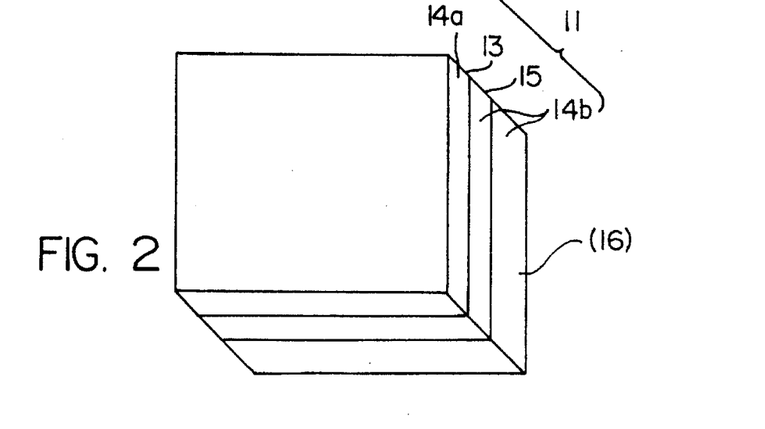
FIG. 2 shows a contraceptive device made of a laminate of film layers.

In FIG. 2, another version of the film device employs a laminate 11 of film layers. A first film layer 13 is made of, for example, a faster dissolving polymer material for release of a drug material 14a. A second film layer 15 is made of slower dissolving polymer material for release of more drug or another drug material 14b in combination, for example, a spermicide and an anti-infective or anti-inflammatory medication. A third (and additional) layer(s) 16 with additional drug can also be employed for sustained release of the drug. In place of film layers which have not been foamed, it is possible, and often preferred to form the laminate of foamed or combinations of foamed with non-foamed layers as a way of readily controlling the dissolution rate of the laminate. Thus, a composite of desired release properties and agent materials is obtained.

In FIG. 3, the film or film layers are used to form a contraceptive device 20 having the shape of a conventional contraceptive sponge or diaphragm. The film can have a thickness, for example, of from 25–500 mils, sufficient to ensure that the resulting structure will have some degree of turgidity and shape memory so that it can be properly placed and positioned in front of the cervical area. The requisite thickness can be obtained through multiple layers, or by foaming the film layer with gases or both. The structure can be formed by molding the polymer matrix or by cutting from pre-formed sheets. By comparison, a conventional diaphragm or sponge can have a similar thickness. Due to the thickness of the film and the lack of any rigid members, the contraceptive device 20 can be readily collapsed into a small, narrow shape and inserted in the vagina by hand without any discomfort to the user. Once it is positioned in the cervical area, the turgidity and shape memory allow the film structure to spread out and adhere to the moist walls of the vaginal tract. The agent material to be locally administered in the vagina, such as spermicide, is distributed throughout the film, as indicated in the figure by the dots 21. The dosing regime may include an antifungal/yeast medication.

FIG. 3 also shows the preferred feature of a dissolvable flexible rim 22 incorporated in the diaphragm. The dissolvable rim is an integral part of the device similar to a conventional contraceptive sponge or diaphragm. The rim is also made from the same polymer materials as the dome or body portion of the device. It is incorporated either by rolling the film into a rim, or cutting a thicker foamed portion of the film, or by molding a thicker foamed portion in the unit. In this manner, the device is formed as a barrier film contraceptive that is inserted in the same way as conventional sponge or diaphragm. However, after use once the sponge or diaphragm dissolves, no removal is necessary.

In practice of the present invention, the vaginal device of FIG. 3, which is in the solid state, is self inserted into the vagina. In about 2–3 minutes after insertion and frequently in as little as 5 seconds after contact with the fluids of the vagina, the device begins to dissolve. Depending upon the nature of the polymeric makeup the device continues to dissolve over a period of up to 24 hours during which time it can be used to controllably release a drug or combination of drugs over a sustained period of time. Thus once the present device is inserted, the user does not have to be concerned about removal. During the dissolving state the device prevents sperm passage while any spermicidal drug present kills the sperm in the vagina.

Figure 5:
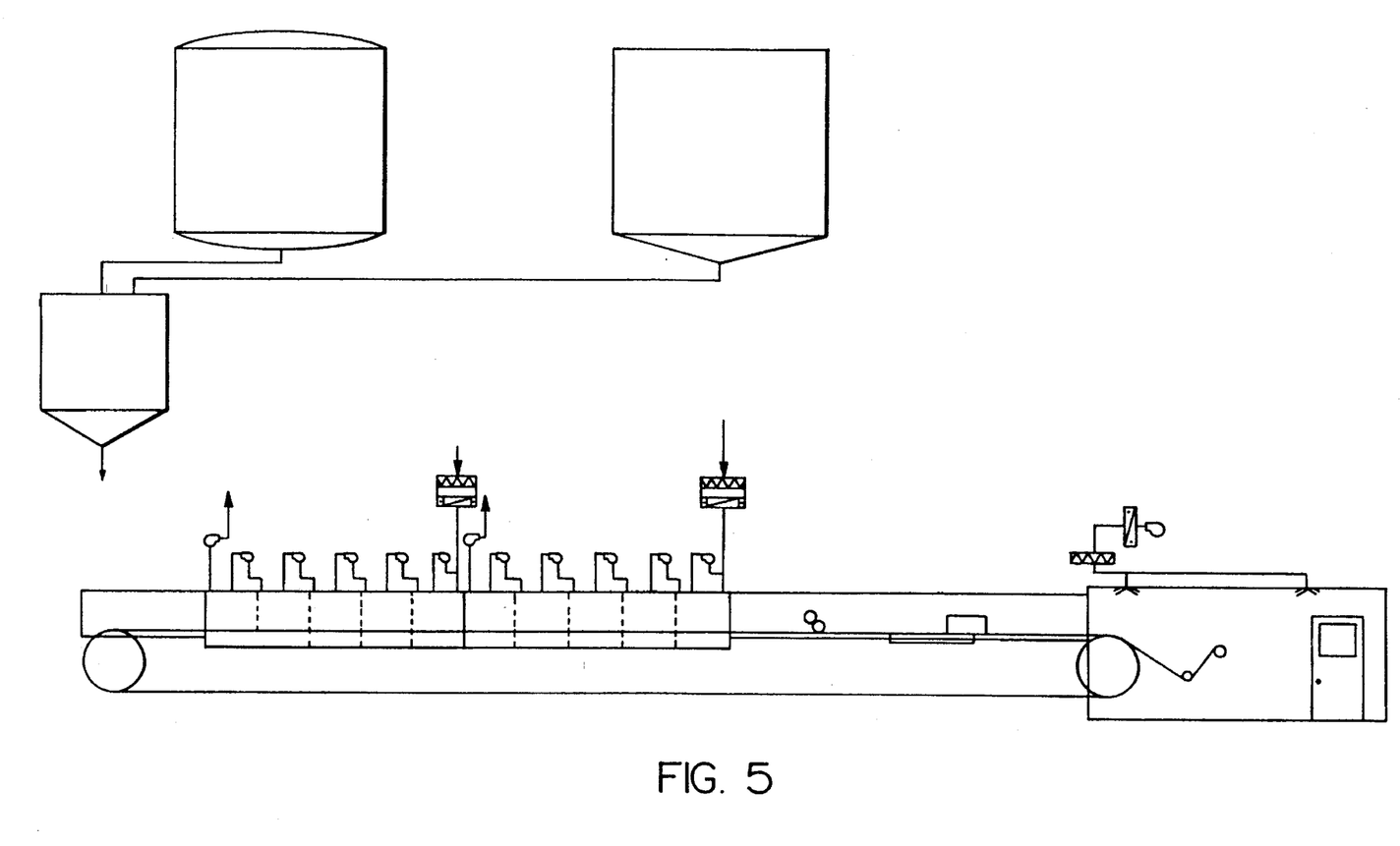
FIG. 5 is a flow sheet showing an embodiment of the process of the invention.

FIG. 5 illustrates in flow sheet form, various embodiments of the process of the invention. There are five casting lines each of which has a 48" width stainless belt with a center-to-center length of 200 feet. A drying/cooling tunnel of 126 ft. length is located immediately after the casting area. Heat is applied by underbelt steam and overbelt hot air—both are adjustable. The line has the capability of applying a coating to the top side of the sheet product. Humidification of the finished sheet product is also possible. Sheet is removed from the belt in mill roll form. The equipment can be modified to foam the polymer material prior to casting and to remove product in sheet or flake form, thresh and micropulverize the product.

The size of the intra-vaginal device is standardized. One size is suitable for use. The devices may be manufactured in mass quantities at a low cost by standard methods such as molding and casting.

Figure 4:
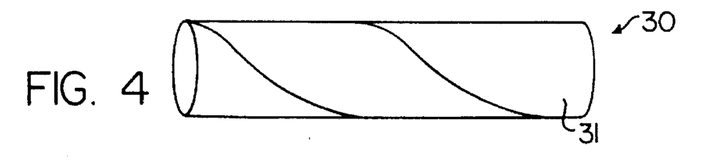
FIG. 4 shows a contraceptive or medication applicator formed by a roll of dissolvable film.

FIG. 4 illustrates the invention in the form of a tubular applicator 30 made of the same selected dissolvable polymer materials. Such a device can be made by rolling a sheet of film 31 into a tubestock which is then cut to size. The device can then be used to facilitate the insertion of drugs or other devices, e.g., tampons, sponges, etc., into the vagina. Once it is discarded, it is dissolved readily in cold water, leaving no plastic or paper materials to clog plumbing or remain as unsightly debris in waterways.

The dissolvable films and devices described herein can be made at a substantially lower cost than conventional devices and do not have the associated problems of removal, cleaning, reuse, or refitting, as compared to conventional sponges and diaphragms. It can also offer barrier protection and retention with timed release properties that go beyond that offered by conventional contraceptive devices, such as foams, gels, inserts, etc. The films are also convenient, easy to apply and use and not messy as compared with conventional products.

A basic process for manufacture of the film will now be described. The desired agent materials are dissolved in a base polymer material, e.g., hydroxypropyl methyl cellulose with a plasticizer in a premix tank. The mixture is then spread evenly to a desired thickness, e.g., for a film, 3.0 to 4.5 mils thick, or for a sponge, 250 mils thick, over a metal sheet or band and passed through a drying oven at a controlled temperature, typically 130°–140° F. The film is then released from the metal drying sheet or band and rolled onto a pickup spool. The film may include coloring agents, fragrance, slip agents, antimicrobials, opacifying agents, etc., as needed.

The spool is used as a supply to a slitting operation to form the film into rolls of 2 inch (5 cm) widths. The film contraceptive units are then formed in a cutting and trimming operation using the 2-inch rolls. Each film unit is packaged as a small sheet or "leaf" in a sealed envelope and boxed in quantity for sale. A single 2-inch wide film, 3 mils thick, can contain the appropriate amount of spermicide for contraception. A film made of hydroxypropyl methyl cellulose and glycerin is a very safe product of natural materials, except for the active agent and any additives used.

An example of the manufacture of a specific film follows:

Benzalkonium chloride Film containing 19 mg of benzalkonium chloride

All of the ingredients are mixed together in a blender until just blended.

| | |
|---|---|
| hydroxypropyl methyl cellulose | 52.5% |
| glycerine | 37.5% |
| benzalkonium chloride (50% aqueous) | 10.0% |
| | 100.0% |

Once blended the mixture is aerated by bubbling nitrogen into the blended mixture until a foamed web is formed. The term "web" as used herein describes an intimate admixture of the glycerine, hydroxy propyl methyl cellulose, added ingredient(s) and inert gas which has a frothy, i.e., foamed appearance. By weight this amounts to less than 1% of the total product. The resultant foamed web is then poured onto a glass plate and spread to an even 3 mil thick film covering the surface of the glass. The glass plate is then allowed to dry, approximately 20 minutes at 160° F. in a temperature regulated oven. After drying the glass plate is removed from the oven. The film is lifted from the glass surface and stored in clean plastic packaging until ready for use. This procedure was utilized to produce two inch square films each containing 19 mg benzalkonium chloride and about 190 mg in weight.

The above procedure was repeated for producing larger quantities of film. The same formula was blended in a sanitized mixing tank with a blending paddle until a homogeneous mixture resulted. Just prior to delivery to the casting area, the mixture was aerated with nitrogen to form a foamed web. This is accomplished by the addition of the nitrogen into a closed system which contains opposing mixing blades. The nitrogen is retained in the formula which is then delivered to the casting area. At the casting area, the mixture is poured onto the surface of a continuous stainless steel casting belt (4 feet wide) and spread to a constant 3 mil thickness. The continuously moving steel belt enters a dryer section where the film is dried for 20 to 40 minutes. After exiting from the dryer section, the film is wound on a spool for storage under sanitary conditions. The four foot wide film is then slit to two inch rolls for further cutting to form 19 mg benzalkonium chloride containing two inch by two inch films (190 mg in weight) and then subsequently individually packaged.

The attached engineering drawing describes the process.

The film may also be formed as a tampon applicator or a contraceptive/antifungal sponge applicator. In this case, the film is passed through a winding operation to roll the film into tubular form. The tubes are cut to the desired length to form tampon applicators. After tampon insertion, the applicator can be discarded by flushing down the toilet. The discarded applicator will dissolve in water in a short time, so that the problem of solid waste or unsightly flotsam on beaches and waterfront areas is entirely avoided. The user has the benefits of a high gloss, plastic applicator feel for ease of insertion.

The dissolvable element containing a spermicide and/or medication may alternatively be ground into granular or finely divided form and incorporated with a vaginal insert such as a tampon or suppository. The granules provide the benefit of desirable timed release properties in conjunction with the dissolving of the polymer material. Two or more types of dissolving polymer materials may be used to obtain staggered release characteristics over different periods of time.

The dissolvable film, as used for contraception or internal delivery of medication in accordance with the present invention, thus has a number of advantages over conventional contraceptives and tampon and sponge applicators. It is fully dissolvable and environmentally safe for disposal, and does not require removal, cleaning refitting or replacement. It is made of natural, food grade materials for safe internal use, and can be manufactured free of any irritant or toxic chemicals. Tests show that the film can be made to dissolve to deliver the agent in less than half the time required for other contraceptive film devices. It is very convenient and not messy to apply and use, and will not stain clothing as with foams, creams and gels. As a contraceptive film, it causes no irritation and does not interfere with the sensation of the sexual partners. It can be readily inserted by hand and does not require an applicator. The film can be used at the same time to administer desired medications in internal areas of the body. It may also be ground and incorporated In a vaginal suppository or other device to effect a timed release action.

Various test procedures were carried out for determining dissolution times and assessing effect of humidity.

The test procedures and results follow:

A standard dissolution assay was developed. The procedure was to immerse the film (2×2 inch) in 1000 ml saline (98.6° F.) in a beaker set on a magnetic stirrer and timing that period of time for the film to be completely dissolved, i.e. the film completely breaks apart leaving no structural integrity.

The dissolution assay was applied to several different experiments.

(1) A comparison was made of 2 experimental films and VCF a commercial film.

Values are that period of time necessary for in vitro dissolution of the agent or device being tested.

| No. of tests | Product | time range seconds | mean time seconds | time range |
|---|---|---|---|---|
| 3 | VCF | 20–25 | 23.3 | |
| 3 | AL 488-53-1* | 8–12 | 9.7 | |
| 3 | AL 488-52-1** | 8–11 | 9.7 | |

VCF 2 × 2 inch commercial film
*Allendale Labs 488-53-1, 2 × 2 inch experimental film, 19 mg BZK Formula as follows: hydroxypropyl methyl cellulose 52.5%, glycerine 37.5%, benzalkonium chloride 10.0% and nitrogen to form web <1%.
**Allendale Labs 488-52-1, 2 × 2 inch experimental film, 25 mg BZK Formula as follows: hydroxypropyl methyl cellulose 50.25%, glycerine 37.5%, benzalkonium chloride 12.25% and nitrogen to form web, <1%.

(2) Comparisons were also made of a laminate of 2 films with the non laminated base film according to the previously described procedure.

Values are the period of time in seconds for in vitro dissolution of the agent or device being tested.

| No. of tests | Product | time range seconds for single layers | mean time seconds | mean time seconds for bilaminate layers | range seconds |
|---|---|---|---|---|---|
| 2 | 485-42-1* | 10–11 | 10.5 | | |
| 2 | 485-46-1D** | 4–5 | 4.5 | | |
| 2 | Bilam*** | 4–5 | 4.5 | 9–13 | 11 |

*Allendale Labs 488-42-1 aerated film Formula as follows: hydroxpropyl methyl cellulose 36%, glycerine 29%, 100 mg nonoxyl-9 35%, and nitrogen to form very light web <0.001%.
**Allendale Labs 485-46-1D aerated film Formula as follows: hydroxypropyl methyl cellulose 36%, glycerine 29%, 100 mg nonoxynol-9 35% and nitrogen to form web,

| No. of tests | Product | time range seconds for single layers | mean time seconds | mean time seconds | range seconds for bilaminate layers |
|---|---|---|---|---|---|

***Allendale Labs Bilam-1 (HPMC/H$_2$O 75:1 adhesive) (Bilam is a laminate of 485-42-1 and 485-46-1D).

The bilaminate product dissolved in two phases, i.e. the first layer dissolved within 4.5 seconds. The second layer dissolved at 11 seconds resulting in a delayed dissolution. The results indicate that lamination with a hydroxypropyl methyl cellulose water adhesive will form a laminate with extended dissolution characteristics while still retaining the immediate dissolution characteristics. The data can be applicable to an immediate/extended release of agent in vivo.

(3) Dissolution times were obtained and compared for an aerated polyvinyl alcohol film with a film composed of a mixture of two grades of aerated polyvinyl alcohol, by the dissolution assay.

Values are that period of time in seconds for in vitro dissolution of the agent or device being tested.

| No. of tests | Product | time range seconds | mean time seconds |
|---|---|---|---|
| 2 | A-10-2* | 22–26 | 24 |
| 2 | A-10-3** | 9–11 | 10 |

*A-10-2, A standard aerated film composed of cold water soluble polyvinyl alcohol. Formula as follows: polyvinyl alcohol 99% hydrolyzed) 55%, glycerine 45% and nitrogen to form web, <1%.
**A-10-3 a polyvinyl alcohol film, aerated composed of both the above cold water-soluble film as well as a medium range soluble film. Formula as follows: polyvinyl alcohol (99% hydrolyzed) 10%, polyvinyl alcohol (80% hydrolyzed) 45%, glycerine 45% and nitrogen to form web, <1%.

The cold water soluble film was shown to dissolve in 24 seconds. By adding another grade of polyvinyl alcohol to the formulation, the dissolution characteristics were altered, i.e. the resultant film dissolved more readily. Thus demonstrating the ability to alter dissolution times by adding various grades of polyvinyl alcohol to the base formula.

An assay was developed to determine the effect of short term exposure of the films to a humid environment as it is known that humidity affects various types of films. The procedure employed follows:

Water is placed in a bell jar and allowed to reach saturation.

A series of film strips are folded and suspended near the top of the jar and observed over a period of time.

At intervals of 15 minutes, the films are examined to determine tackiness and returned to the bell jar for further "development" in the humid atmosphere.

Values are the period of time, in minutes, at which point tackiness is first observed by tactile sensation.

| No. of tests | Product | Time range minutes | Mean time minutes |
|---|---|---|---|
| 3 | PVA* | 45–60 | 50 |
| 3 | HPMC** | 90–120 | 110 |

PVA polyvinyl alcohol film, 2 × 2 inch square aerated Formula as follows: polyvinyl alcohol (86% hydrolyzed) glycerine 29% and nitrogen to form web <1%.
**HPMC hydroxypropyl methyl cellulose film 2 × 2 inch square, aerated Formula as follows: hydroxypropyl methyl cellulose 71% glycerine 29% and nitrogen to form web, <1%.

Results of this experiment indicate that hydroxypropyl methyl cellulose is more resistant to the effects of high humidity than polyvinyl alcohol. This resistance will yield a film more readily resistant to high humidity conditions and minimize the need for extraordinary packaging requirements.

Numerous variations are of course possible in light of the principles and examples disclosed above. All such variations are intended to be included within the entire spirit and scope of invention, as defined in the following claims.

I claim:

1. A method for the delivery of an agent material into a body cavity, using a device characterized by improved heat and humidity stability of up to 140 degrees F. and up to 97% respectively, said device comprising at least one dissolvable film formed from a member selected from the group consisting of polyvinyl alcohol, polyethylene oxide, hydroxypropylmethyl cellulose and mixtures thereof, at least one of said films having distributed throughout an inert gas, said agent material being incorporated in said dissolvable film, said device dissolving at the temperature of said body cavity in the presence of the moisture naturally present in said body cavity to release said agent material, said method comprising introducing said device into said bodily cavity, whereby on dissolution of said film said agent material is delivered into said bodily cavity.

2. A method according to claim 1 wherein said film is formed of a mixture of at least two of said group members.

3. A method according to claim 1 wherein said film is formed of a mixture of different grades of one of said group members.

4. A method according to claim 1 wherein said agent material is a spermicide, said device is adapted for use as a contraceptive and said method comprises inserting and positioning said device in the vagina.

5. A method according to claim 1 wherein said agent material is a medication, said device is adapted for use for the delivery of said medication and said method comprises positioning said device in the body cavity where the medication is to be delivered.

6. A method according to claim 1 wherein in said device, said film is a laminate formed of at least two film layers, each of said layers comprising a group member characterized by different dissolution properties.

7. A method according to claim 1 wherein said film is a laminate formed of at least two film layers, each of said layers comprising the same group member, but each characterized by a different temperature dissolution property.

8. A method according to claim 1, wherein said body cavity is the vagina, rectum, mouth, nose, ear or eye.

9. A method according to claim 8, wherein said body cavity is the vaginal vault and the device is of sufficient thickness so that it functions as a physical barrier.

10. A method according to claim 1 wherein the dissolution rate of said film is adjusted by varying the amount of inert gas introduced into said film.

11. A method according to claim 1 wherein said agent material is a member selected from the group consisting of anti-infectives, ant-inflammatories, estrogenic steroids, progestational agents, protaglandens, coronary vasodilators, antitussives, antihistamines, anesthetics, and decongestants.

12. A method according to claim 8 wherein said body cavity is the mouth.

13. A method for topical delivery of an agent material to an external body area, using a device characterized by improved heat and humidity stability of up to 140 degrees F. and up to 97% respectively, said device comprising at least one dissolvable film formed from a member selected from the group consisting of polyvinyl alcohol, polyethylene oxide, hydroxy propyl methyl cellulose and mixtures thereof, at least one of said films having distributed throughout an inert gas, said agent material being incorporated in said dissolvable film at the temperature of said body cavity in the presence of the moisture naturally present in said body cavity to release said agent material, said method comprising applying said device onto an external body area, whereby on dissolution of said film said agent material is delivered topically to said external body area.

* * * * *